United States Patent [19]
Fay

[11] Patent Number: 5,617,206
[45] Date of Patent: Apr. 1, 1997

[54] COMPACT LASER DIODE MONITOR USING DEFINED LASER MOMENTUM VECTORS TO CAUSE EMISSION OF A COHERENT PHOTON IN A SELECTED DIRECTION

[75] Inventor: Theodore D. Fay, Mission Viejo, Calif.

[73] Assignee: PHI, Applied Physical Sciences International, Mission Viejo, Calif.

[21] Appl. No.: 566,965

[22] Filed: Dec. 4, 1995

[51] Int. Cl.$^6$ .................... G01J 3/42; G01J 3/44
[52] U.S. Cl. .......................... 356/320; 356/301
[58] Field of Search .................. 356/311, 301, 356/39, 320; 128/633; 250/574

[56] References Cited

U.S. PATENT DOCUMENTS

| | | | |
|---|---|---|---|
| 3,802,779 | 4/1974 | Regnier et al. | 356/301 |
| 3,914,055 | 10/1975 | Wolga et al. | 356/301 |
| 4,084,100 | 4/1978 | Begley et al. | 356/320 |
| 5,243,983 | 9/1993 | Tarr et al. | |
| 5,303,710 | 4/1994 | Bashkansky et al. | |

OTHER PUBLICATIONS

Gilmore et al. Quantitative Detection of Environmentally Important Dyes . . . Applied Spectroscopy vol. 49 No. 4 1995 p. 508.
Toleutav et al. Broadband (1000 cm$^{-1}$) multipley CARS spectroscopy: . . . Applied Physics B 59, 369–375 1994.
Bengtsson et al. Combined Vircational & Rotational CARS for . . . Applied Spectroscopy 49, 2, 188–192, 1995.
Hobbs et al. Scintillator–Based Nanosecond Light Sources . . . Applied Spectroscopy 49, 1, 15–19, 1995.
Bright, Frank V. Modern Molecular Fluoroscence Spectroscopy Applied Spectroscopy 49, 1, 14A–19A, 1995.

*Primary Examiner*—K. Hantis
*Attorney, Agent, or Firm*—Walter A. Hackler

[57] ABSTRACT

A compact laser diode monitor for measuring concentrations of individual atomic and molecular species in both gaseous and semitransparent fluids, includes a first diode laser having an output for resonantly exciting a first selected electronic transition of a specific atomic or molecular species of a sample, and a second diode laser having an output for resonantly exciting a second selected electronic transition of said specific atomic or molecular species of said sample. A difference between said first and second frequency outputs is equal to a vibrational energy level difference of the specific atomic or molecular species. Further said first and second frequency outputs are simultaneously directed into said sample, with selected momentum vectors in order to cause the selected atomic or molecular species to emit a coherent photon signal in a selected direction having a frequency equal to twice the first frequency output minus the second frequency output. A detector is provided for receiving the emitted coherent photon signal and spectrally analyzing the emitted coherent photon signal.

36 Claims, 3 Drawing Sheets

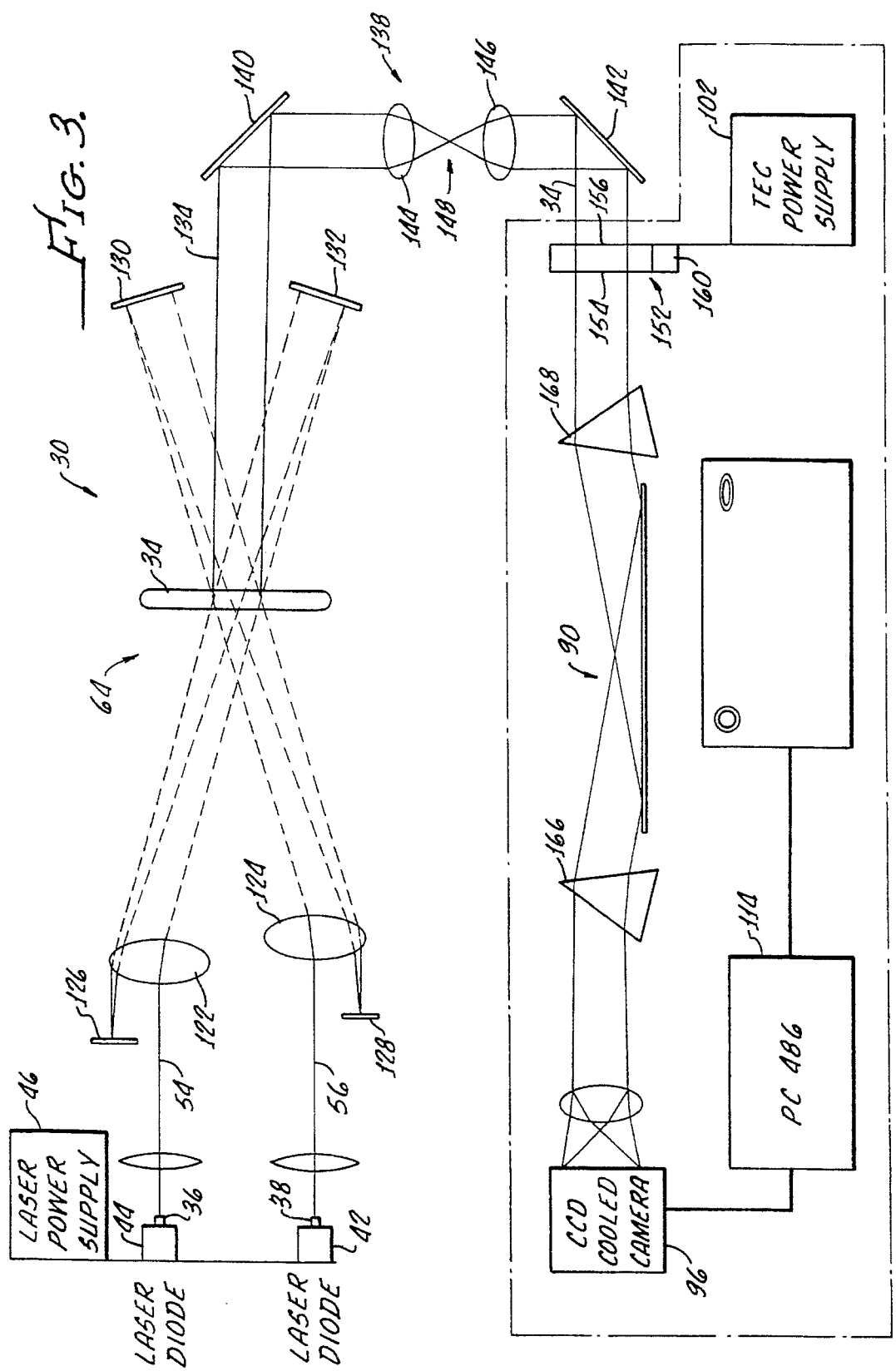

COMPACT LASER DIODE MONITOR USING DEFINED LASER MOMENTUM VECTORS TO CAUSE EMISSION OF A COHERENT PHOTON IN A SELECTED DIRECTION

The present invention generally relates to apparatus and methods for the optical examination of scattering and fluorescent mechanisms of atomic and molecular species utilizing logic time and wavelength spectroscopy. More particularly the present invention is directed to a compact laser diode monitor for measuring concentrations of individual atomic and molecular species in both gaseous and semitransparent fluids.

Detection and measurement of concentrations of small amounts of individual atomic and molecular species include a multitude of government and industrial trial applications. Regulatory agencies have a vital interest in the field of this invention for many non-military purposes such as, for example, monitoring toxic chemicals, both natural and man-made. Military applications, of course, would include monitoring the nuclear, chemical, and biological environments as they relate to the proliferation of weapons and the use of same.

Further commercial applications for the present invention may be found in a great number of industries tries, such as oil refineries, in determining the release lease of toxic materials; the semiconductor industry, in which qualitity control of toxic materials is of utmost importance; the paper and pulp industries for monitoring organic and sulfur toxic chemicals. In addition, such monitors may be used to advantage for the improvement of the efficiency of auto engines, single stage aircraft turbines, as well as multistage turbines for electrical power production.

Heretofore, researchers have utilized the adsorption, scattering, the re-emission of light medium for determining the identity of atomic molecular components within a medium. However, most, if not all, of these developments have entailed the use of very expensive and large equipment which precludes their use in a multitude of applications hereinabove described.

Many excellent basic texts describing Raman spectroscopy and laser fluorescence now exist. For example, *Practical Raman Spectroscopy*, Gardianer and Graves, 1989, Springer-Verlag, Berlin and New York; *Analytical Raman Spectroscopy*, Grasselli and Bulkin, 1991, Vol. 114 of *Chemical Analysis*, John Wiley & Sons, Inc., New York; and *Topics of Fluorescent Spectroscopy*, Lakowcz, 1991, Plenum Press, New York, Vols. I, II, III. All of these references are incorporated herein in toto for the purpose of providing a summary of the application of Raman scattering to molecular bond analysis in unknown samples.

The present invention provides methods and apparatus to separate Raman and fluorescent mechanisms in order to identify and detect small concentrations of atomic and molecular species. For example, the present invention may be used to detect small concentrations of pollutants against the background of many atmospheric species, whose partial pressures and atmospheric mixtures are larger by 4 to 9 orders of magnitude.

SUMMARY OF THE INVENTION

The method and apparatus of the present invention utilizes two laser diodes having frequencies resonant with the selected electronic transitions of a specific atomic or molecular species, as will be hereinafter described in greater detail. At least one of the laser diodes must be tunable in order that a difference be established between the laser frequencies which equals a selected vibrational energy level difference so that an emitted signal emerges coherently in a single, parallel direction.

More particularly, a compact laser diode monitor, in accordance with the present invention for measuring concentrations of individual atomic and molecular species in both gaseous and semitransparent fluids generally includes a first diode laser, which provides a means for exciting a first selected electronic transition of a specific atomic or molecular species of a sample. In this instance, the first laser has a first frequency output resonant with the first selected electronic transition.

Importantly, a second diode laser provides means for exciting a second selected electronic transition of the specific atomic and molecular species of the sample with the second laser having a second frequency output resonant with the second selected electronic transition. Most importantly, a difference between the first and second frequency output is equal to a vibrational energy level difference of the specific atomic or molecular species.

Means are provided for simultaneously directing the first and second frequency outputs from the lasers into the sample with selected momentum vectors in order to cause the selected atomic or molecular species to emit a coherent photon signal in a selected direction, having a frequency equal to twice the first frequency output minus a second frequency output.

Means are also provided for detecting the emitted coherent photon signal and spectrally analyzing same.

More particularly, a means for directing the first and second frequency outputs into the sample includes a lens system for causing the first and second frequency outputs to converge onto the sample and a mirror configuration provides means for causing the first and second frequency outputs passing through the sample to reenter the sample a selected number of times, for example, up to at least 100 or more.

Importantly, the lens system in the mirror configuration are spaced apart from one another no more than 10 centimeters which enables the construction of optics having a volume no greater than about 1,000 cc and a mass of less than 1 kilogram, as will be hereinafter discribed in greater detail.

In addition, optical means may be provided and disposed between the sample of the means for detecting the emitted signal for reducing the background fluorescent signal which is generated by the sample. This is accomplished by reducing the amount of the fluorescent signal entering the means for detecting the emitted coherent photon signal.

Still more particularly, the means for detecting the emitted photon signal may include a tunable-wavelength filter which may be tunable by application of heat thereto. In that regard, the tunable wavelength filter may comprise a Fabry Perot device, having two spaced apart flat parallel plates with an organic chemical disposed between the plates.

As will be discussed hereinafter in greater detail, the organic chemical utilized preferably has an index refraction change rate with temperature; more specifically, an index of refraction which decreases with increasing temperature.

Alternatively, the tunable wavelength filter may comprise a solid inorganic material having index refraction change rate in temperature. In one embodiment of the present invention, a means for detecting the emitted coherent photon signal may include dispersive means, disposed for receiving the output from the tunable wavelength filter, for selecting fringes in the Fabry Perot output for detection.

More particularly, the means for detecting the emitted coherent photon signal may include a detector array for receiving the selected fringes and producing an electrical signal corresponding thereto.

In one embodiment, the means for detecting the emitted coherent photon signal may include a broad band filter for isolating a single order of fringe output from the Fabry Perot device. Specifically, the broad band filter may comprise an acousto-optic tunable filter.

Alternatively, in accordance with the present invention, a compact laser monitor may be provided for comparing concentrations of individual atomic and molecular species in both gaseous and semitransparent fluids.

In this instance, a first laser diode provides means for exciting a first selected electronic transition of a specific atomic or molecular species of a sample and a standard with the first laser having a first frequency output resonant with the first selected electronic transition. In addition, a second diode laser is utilized to provide means for exciting a second selected electronic transition of the specific atomic or molecular species of the sample and the standard, with the second laser having a second frequency output resonant with the second selected electronic transition. A difference between the first and second frequency output is equal to the vibrational energy level difference of the specific atomic or molecular species.

In addition, means are provided for simultaneously directing the first and second frequency outputs into the sample and standard, with selected momentum vectors in order to cause the selected atomic or molecular species in the sample and the standard to emit coherent photon signals in selected directions, having a frequency equal to twice the frequency output minus the second frequency output. Means are also provided for detecting the emitted coherent signals and comparing them.

A method in accordance with the present invention for monitoring concentrations of individual atomic and molecular species in both gaseous and semitransparent fluids includes steps of directing a first laser having a frequency resonant with a first selected electronic transition of a specific atomic or molecular species into a sample comprising the specific atomic or molecular species.

Simultaneously, a second laser is directed at the sample in order to cause the selected atomic or molecular species to emit a coherent photon signal in a selected direction and detecting the emitted coherent photon signal.

BRIEF DESCRIPTION OF THE DRAWINGS

The advantages and features of the present invention will be better understood by the following description when considered in conjunction with the accompanying drawings in which:

FIG. 3 is a representation of the present invention further detailing the present invention, in particular features of its compact optic system and of coherent Raman signal from background emissions, such as fluorescence.

DETAILED DESCRIPTION

Figure 1:
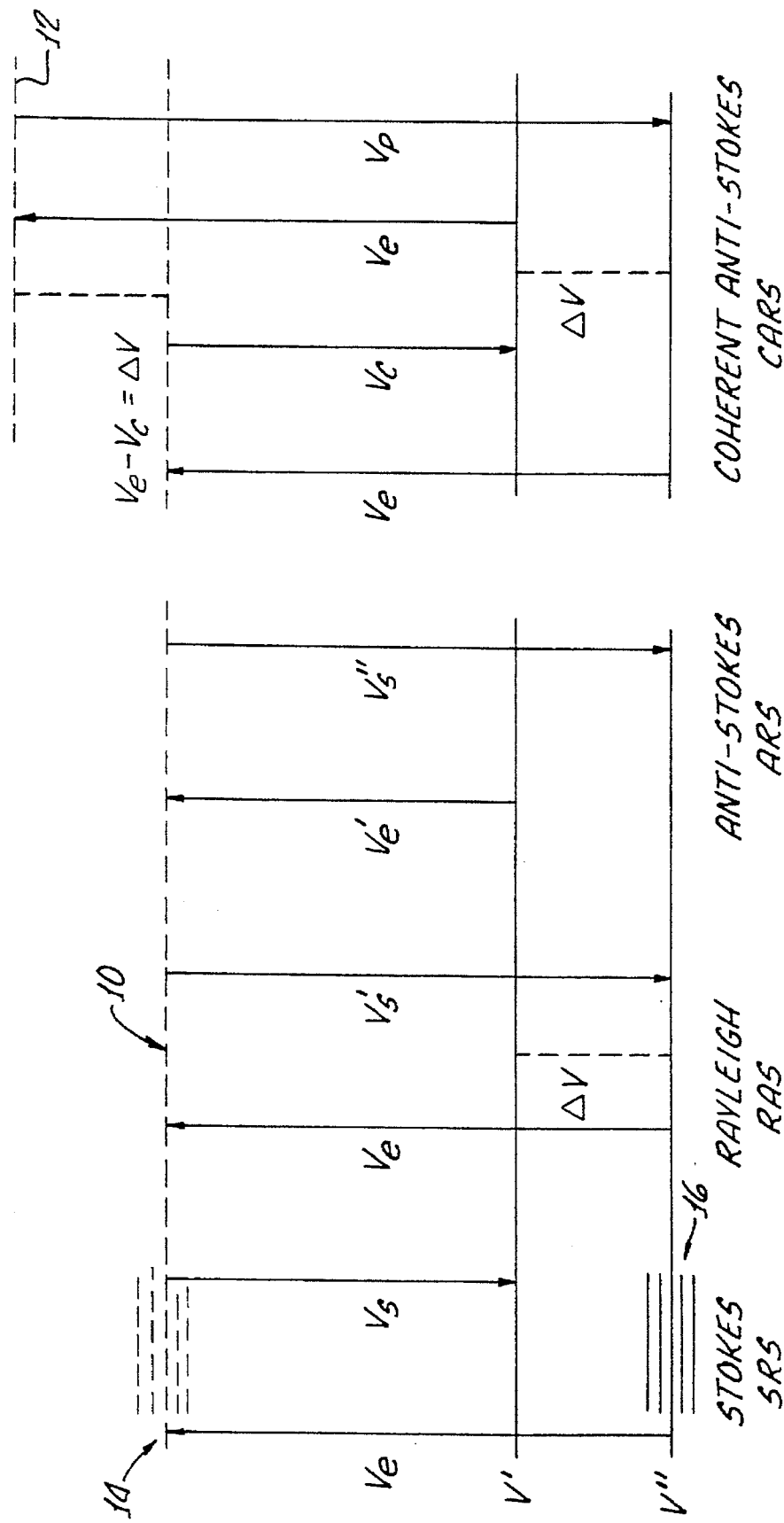
FIG. 1 is a simplified energy-level diagram of an atomic or molecular species in the scope of describing the mechanisms of the present invention.

FIG. 1 presents a simplified energy-level diagram for hypothetical atomic or molecular species. The atomic or molecular species, i.e., medium, represented by the energy-level diagram of FIG. 1, when radiated with energy in a frequency range which excites a vibrational energy level. Various types of Rayleigh and Raman scattering occurs, and the emitted Raman spectrum can be spectrally analyzed to identify the medium.

FIG. 1 is useful in describing the various scattering mechanisms medium. In FIG. 1, v" represents the ground vibrational level of the represented atomic or molecular species. The first excited vibrational energy level is identified by the line v'. The difference between these vibrational energy levels, $\Delta v = v' - v''$ are specific to each molecule. Stokes resonance scattering (SRS) occurs when the medium is radiated with a frequency $v_e$.

This excites the electronic state of the medium to a virtual continuum level indicated at the dashed line 10. Energy of a different frequency is emitted, as scattered radiation, with the frequency $v_s$. This describes a normal Raman scattering phenomenon which utilizes one laser for irradiating a medium with a frequency $v_e$.

For illustrative purposes, Rayleigh scattering (RAS) is also illustrated in FIG. 1. In this mechanism, the absorbed laser frequency $v_e$ causes an electronic transition to the virtual continuum level 10; however, the emitted light occurs at the same frequency $v'_s$. Raman scattering differs from Rayleigh scattering in the frequency of the scattered light. Rayleigh scattering produces scattered light with the same frequency as the unscattered and, although not shown in FIG. 1, bears a definite phase relationship thereto.

In the Stokes Raman scattering illustrated in FIG. 1, the scattering is incoherent and has a random alteration in phase.

Another set of spectral lines, known as anti-Stokes Raman scattering (ARS) occurs when the absorbed energy $v'_e$ causes a transition to the virtual continuum level 10, and a subsequent scattered photon $v''_s$ which is greater in energy than the absorbed energy is emitted. This is illustrated in FIG. 1 under the heading "Anti-Stokes".

Typically, the Stokes lines are stronger since the ground states are stable and normally have higher population fractions. It is well known that the cross-sections for Stokes, anti-Stokes and Rayleigh scattering all increase as the fourth power of the laser frequency used in the experiment. However, unfortunately, for the analyst, Raman scattering is much less probable than laser fluorescence by a factor of about 8 billion (typical cross-sections are $10^{-29}$ and $10^{-19}$ cm$^2$ respectively) in the near infrared (1,000 nm).

At these wavelengths, the fraction of molecules that fluoresce with electronic and vibrational transitions is lowest in the spectrum. At many other wavelengths, UV, visible, IR, the very strong laser fluorescence of each molecule in a simple medium creates a complex set of spectral lines in a number of different wavelengths. Thus, a sample spectrum with many molecules will often have a complex and contaminated spectrum requiring high resolutions spectroscopy in addition to the laser. Further, Rayleigh scattering creates its own background noise at the laser frequency with a cross-section of about $10^{-25}$ cm$^2$.

Accordingly, both Rayleigh scattering and fluorescence will contaminate the emitted spectrum. Fluorescent contamination is least severe at diode laser wavelengths in the infrared (3,000–30,000 nm) but both are very severe in the UV (40–400 nm). At these wavelengths, most molecules have either their fundamental vibrational bands (infrared) or electronic transitions (UV). As hereinabove noted, the present invention enables detection of small concentrations of a specific atomic and molecular species against the hereinabove-noted background contamination.

Another common Raman scattering technique is the utilization of lasers having frequencies which correspond precisely to an energy level difference of the electronic transition of a particular molecule. Each electronic transition of the molecule has many vibrational and rotational sub-bands, represented by the lines 14, 16 in FIG. 1. Accordingly, one of the subtransitions which can occur can coincide with the visible or near infrared laser frequency, provided that a suitable molecule, such as $NO_2$ or $O_3$, has a visible electronic state.

This resonant Raman technique results in cross-sections which are 10,000 times stronger ($10^{-24}$ cm$^2$) than Stokes and anti-Stokes scattering at an off resonance laser frequency. This technique enables the detection of parts per billion of $NO_2$ in the presence of abundant atmospheric species such as $N_2$, $O_2$, $H_2O$, and $CO_2$.

Another well-known technique is known as the hyper Raman effect which is a two-laser version of a Raman scattering technique, which further enhances the Raman cross-section over that of fluorescence for the same molecule. This technique is known as the CSRS in the Stokes form and the CARS in the anti-Stokes form, which stands for coherent Raman scattering (CRS) as opposed to resonant Raman scattering (RRS), herein above discussed.

In this technique, the difference between the two CRS laser frequencies must precisely equal the vibrational energy level difference of each molecule selected for study. Only the difference between the two laser frequencies is critical to both CARS and CSRS. Further, in this technique, one of the lasers is typically pulsed to increase the instantaneous power intensity to the sample. In this technique, the principal hyper Raman scattered light appears at a frequency that is equal to twice the frequency of the first laser minus the frequency of the second.

Figure 2:
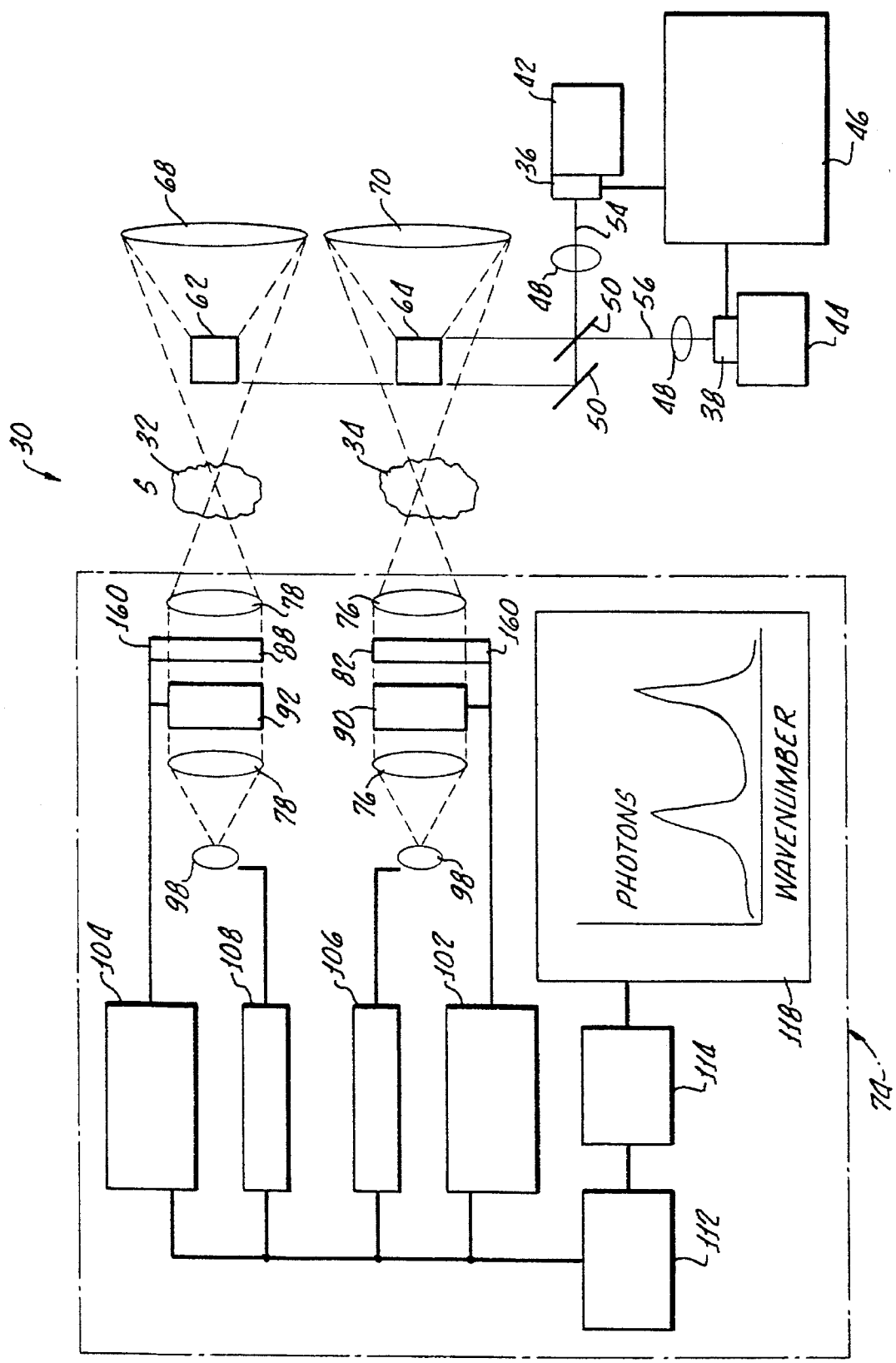
FIG. 2 is a block diagram of one embodiment of the present invention.

The present invention utilizes a pair of precisely tuned lasers in order to provide an optically enhanced Raman scattering cross-section. As shown in FIG. 2, a first laser 36 has a frequency that is precisely resonant with an electronic transition of a molecule of interest. A second laser 38 differs in frequency from the first laser 20 such as described in the CSRS and CARS techniques. Therefore, the frequency difference is equal to the molecular vibrational energy difference.

Moreover, in the present invention, lasers 20, 22 are precisely tuned to the energy level diagram of each molecule, thereby providing an optically enhanced Raman scattering cross-section.

As a result, the emitted signal is coherent and in a selected direction.

In normal Raman scattering, momentum concentration is expressed by the vector equation:

$Ks=Ke-Ka$

This vector equation represents three scalar equations, one for each of the three dimensions. The vector momentum of the single laser is Ke and the vector momentum of the molecule is Ka.

The absolute value of Ka is equal to the vibrational energy difference of $\Delta v$ of a given on FIG. 1. The signal photons from the scattering are represented by the vector Ks.

No unique solution is possible with this vector equation because it has only three scalar equations for the five unknowns, namely, $r_s$, $\Theta_s$, $\phi_s$, $\Theta_a$, and $\phi_a$ where $\Theta_s$ and $\phi_s$ are the angles that define the signal direction, $\Theta_a$ and $\phi_a$ are the angles that define the vector momentum of the molecule and $r_s$ is the value of the signal vector. Consequently, in normal Raman scattering, a signal will emerge incoherently in a broad cone rather than coherently in a collimated beam.

On the other hand, in accordance with the present invention, the use of two lasers provides two photon momentum exchanges Ke with the molecule momentum vector Ka. These exchanges determine the fixed angle at which the scattered beam emerges as defined by the following equation:

$Kp=Ke-Ka$ where $Ka=Ke-Kc$

Therefore, the vector of the emitted photon Kp is defined since both vectors Ke and Kc are determined by the geometry of the optics as hereinafter described.

As a result, the emitted photon signal defined by the vector Kp is a coherent beam emitted in the direction defined by $\Theta_p$ and $\phi_p$. Because the beam is emitted in a known direction, as contrasted with regular Raman scattering, the higher fraction of the scattered photons can be collected with a proper optical design as hereinafter discussed in connection with FIG. 3.

Turning now to FIG. 2, there is shown in block diagram form a compact laser diode monitor 30 measuring and comparing concentrations of individual atomic and molecular species in both gaseous and semitransparent fluids.

It should be appreciated that while the monitor shown in FIG. 2 is characterized by the fact that irradiation of both a known, or a standard, sample 32 is compared to an unknown specimen or sample 34, the apparatus may be utilized without the reference 32 for measuring and/or detecting concentrations of a neutral species in the sample 34. A separate description of the invention as it may be used without the standard 32 is not represented herewith for the sake of eliminating redundancy in the description of components; however, the present specification is intended to cover all such embodiments since all the features and components thereof are shown in FIG. 2.

In accordance with the present invention, a compact laser diode monitor 30 generally includes a first diode laser 36 which provides a means for exciting a first selected electronic transition of a specific atomic or molecular species of a sample 34 and the standard 32. As hereinafter discussed in greater detail, the first laser 36 has a first frequency output resonant with the first selected electronic transition.

Also provided is a second diode laser 38 which provides means for exciting a second selected electronic transition of the specific sample of a molecular species of the sample 34 and the standard 32. The second laser 38 provides a second frequency output resonant with the second selected electronic transition and as noted hereinabove, a difference between the first and second frequency outputs is equal to a vibrational energy level difference of the specific atomic or molecular species.

The laser diodes 36, 38 may be commercially available with a power of at least 0.5 watts and are selected on the basis of their frequency output for resonant excitation of first and second selected electronic transitions, as hereinabove described. Naturally, wavelengths must be selected having frequency differences which fit the atomic or molecular species under consideration.

As an example, high powered AlGaInAs laser diode (LD) pairs suitable for the present invention are set forth in Table 1, no limitation of the suitable lasers being intended by the suggested pairs.

TABLE 1

| Target Gas Selected | Chemical Bond | Raman $\omega$ (cm−1) | CARS Lasers $\lambda_x$(nm) Laser $\lambda_e$ | Laser $\lambda_c$ | CARS Signal $\lambda_p$(nm) | $\omega_p$(cm−1) |
|---|---|---|---|---|---|---|
| Mustard Gas | CCl,CS | 250 | 675 | 687 | 663 | 15074 |
| Mustard Gas | CCl,CS | 250 | 755 | 770 | 741 | 13495 |
| Agents GA,GB | CP | 715 | 750 | 793 | 742 | 13477 |
| Agents GA,GB | CP | 715 | 793 | 841 | 750 | 13333 |
| Organic, Other | $CH_2$,NO | 2190 | 675 | 795 | 587 | 17020 |
| Organic Agents | CCl,$CH_3$ | 3000 | 675 | 850 | 560 | 17865 |
| $NH_4NO_3$ | $NH_3$ | 3333 | 675 | 870 | 551 | 18136 |

The wavelength of the laser diodes 36, 38 determine the wavelength of the CARS signals set forth in Table 1 since from FIG. 1, the signal wavelength $\lambda_p$ is:

$$\lambda_p=1/\omega_p \text{ with } \omega_p=2\omega_e-\omega_c \text{ and } \omega_x=v_xc/n(\text{air}) \text{ for } x=e \text{ and } c$$

Here $\omega_e$ and $\omega_c$ are the wave numbers of the Table 1 lasers $\lambda_e$ and $\lambda_c$, the corresponding $v_e$–$v_c$ are the FIG. 1 frequencies, c is the velocity of light in vacuum and n(air) is the refractive index of air.

The selection of the laser diodes 36, 38 also must be made in consideration to minimize the background fluorescence of the sources.

The selected lasers 36, 38 are supported by conventional heat sinks 42, 44 and powered by a suitable power supply 46, selected in accordance with the present invention with small-sized mass and cost, as necessary.

A combination of lenses 48 and mirrors 50 provide a means for collimating the laser beams to create identical laser diode beams for directing into the standard sample 32 and unknown sample 34, as illustrated in FIG. 2. As hereinabove noted, if the monitor in accordance with the present invention is to be utilized without a Standard sample 32, the lenses 48 and mirror 50 are selected and positioned for collimating the laser beams 54, 56 only into the sample 34 under investigation.

As hereinafter discussed in greater detail, white cells 62, 64 provide a means for causing the first and second frequency outputs passing through the sample 64, standard 62 to reenter the sample 34 and standard 32 a selected number of times in order to enhance or create an effective larger cross-section for the incident laser beams. The total 100 cm path may be obtained when the beam reenters the sample 34 and standard 32 about 50 times with a 2 cm travel distance. However, it is expected that up to at least 100 passes or more may be utilized.

Optic members 68, 70 provide a means to collect the scattered signal from the white cells 62, 64, as hereinafter discussed in greater detail. In this regard, elliptical mirrors are preferred for the optic members 68, 70 since they have large solid angle capability.

As generally shown by dashed lines in FIG. 2 and, as hereinafter discussed in greater detail, means 74 are provided for detecting the emitted coherent photon signals and spectrally analyzing the emitted coherent photon signal which may include comparison of coherent photon signals from both the sample 34 and the standard 32.

Means for detecting 74 may generally include spectrographic collimating and collection optics such as lenses 76, 78, Fabry Perot filters 82, 84, broad band filters 90, 92, and detectors 96, 98.

As hereinafter presented in greater detail, Fabry Perot control systems 102, 104 provide thermal electric temperature control for the Fabry Perot filters or an acoustic-optic tunable filter (AOTF) substituted therefor, as will be hereinafter discussed.

Conventional control electronic power supplies 106, 108 are provided for the detectors 96, 98, along with an amplifier 112 for the detectors 96, 98 outputs which may be coupled to a data processor 114 to produce an electrical signal and corresponding optical output as represented by the diagram 118.

Turning now to FIG. 3, there is shown in a more diagrammatic format, the compact laser diode monitor 30, in accordance with the present invention, showing for clarity purposes, one channel for directing two laser beams at the unknown sample 34. It should be appreciated that reference numerals in FIGS. 2 and 3 represent similar or identical components of the monitor 30.

In FIG. 3, there is represented lenses 122, 124 which provide a means for directing the first and second frequency outputs 54, 56 to converge onto the sample 34.

As hereinabove previously discussed, mirrors 126, 128, 130, 132 are positioned for causing the first and second frequency outputs 54, 56, passing through the sample 34, to reenter the sample 34 a selected number of times, for example, 50 times for 2 cm spacing between the mirrors 126, 132 and 128, 130.

Although up to about 100 passes or more may be utilized in accordance with the present invention for effectively enhancing the desired Raman cross-section for the entering beams 54, 56 this repeated traverse is not shown in the Figures for the sake of clarity.

Suitable angular positioning of the lenses 122, 124 and mirrors 126, 128, 130, 132 enable the definition of the laser momentum vectors $K_e$ and $K_c$, hereinbefore defined, and associated with the laser beams 54, 56, which cause the emission of the coherent photon signal 134 in a selected direction, as shown in FIG. 3. More particularly, the momentum vectors, $K_e$ and $K_c$, associated with the laser beams 54, 56 may be calculated as follows:

The CARS scattered light momentum vector, $\overline{K}_p$, is proportional to the three orthogonal components: $\overline{K}_p=(+\omega_p \sin \Theta_p \cos \phi_p, \omega_p \sin \Theta_p \sin \phi_p, \omega_p \cos \Theta_p)$ thus $E_p=P_p^c$ where photon energy $E_p$ and momentum $E_p$=momemtum $P_p$=h/2$_p$=h$\omega_p$ h=Planck's constant from equations on page 13, we have $K_p=2K_e-K_c$ $$K_p = (2\omega_e\sin\Theta_e\cos\Theta_e - \omega_c\sin\Theta_c\cos\phi_c,$$
$$2\omega_e\sin\Theta_e\sin\Theta_e - \omega_c\sin\Theta_c\sin\phi_c,$$
$$2\omega_e\cos\Theta_e - \omega_c\cos\Theta_c).$$

Since $\omega_e$, $\omega_c$, $\Theta_e$, $\phi_e$, $\Theta_c$ and $\phi_c$ are determined by the design of the CARS white cell, we can use the third component of the above $K_p$ vector to compute $\cos \Theta_p$ and $\sin \Theta_p$. Then we can use the first and second components of this same vector to compute $\sin \phi_p$ and $\cos \phi_p$. Since $\omega_p=2\omega_e-\omega_c$, the vector is completely determined.

This feature of the present invention has significant advantage in separation of the emitted signal from background noise. That is, since background noise is randomly emitted from the sample, a tremendous geometric advantage is obtained with the production of a coherent signal issuing in a specific direction. The CARS light emerges only at the angles $\Theta_p$ and $\phi_p$. Thus, the detector lens can concentrate this light at a small point on the detector. At the same time, the fluorescent signal emerges at all angles and is dispersed by the optic.

Further enhancement of the emitted signal 13 over randomly directed background is obtained by passing emitted signal 134 through optical means 138 which may include slits 140, 142, lenses 144, 146, and a slit 148, all arranged in conventional manner, optically isolated from the emitted signal 134 from randomly generated background noise.

As shown in FIG. 3, the means 74 for detecting the emitted coherent photon signal 134 includes a spectral analyzer which may be a Fabry Perot filter 82, hereinabove briefly discribed, or a ZnSe prism (ZSP) or an acousto-optic or a tunable filter (AOTF), made from, for example, but not limited to, $O_2$ crystals. These filters do not disturb the focussing characteristics of the CARS signal by the detector lens.

A Fabry Perot is a multi bandpass spectral device consisting of two coated, flat and highly parallel plates 154, 156, generally referred to as etalons. The wavelengths transmitted by the Fabry Perot 152 are a function of the order number m given by the equation:

$$m\lambda = 2nh \cos \theta,$$

where $\lambda$ is the wavelength, n is the refractive index of the medium between the etalons, h is the etalon separation, and $\theta$ is the angle between the input signal and the optic access. A single order isolates a narrow band of wavelength given by the free structural range $\Delta\lambda$ (FSR) of the etalons given by the equation:

$$\Delta\lambda \ (FSR) = \lambda^2/2nh.$$

The Fabry Perot 152 is a very narrow wavelength filter that transmits only wavelengths given by the hereinabove recited equation. The width of the multipass filter band is given by the last recited equation divided by a quantity called the finesse, F, usually about 30, and the filter 152 can be tuned by changing either the refractive index n or h, the space between the etalons 154, 156.

Spacing of the Fabry Perot etalons 154, 156 may be about 0.1 cm, corresponding to a free spectral range of about 4 cm$^{-1}$ or about 100 GHz, depending upon the index of refraction of the material between the etalons 154, 156. This resolution is equivalent to a wavelength resolution of about 0.004 nm at 540 nm or about 0.012 nm at 860 nm if the finesse of the plates is about 25.

In accordance with the present invention, the Fabry Perot is effectively tuned via the use of an organic liquid disposed between the plates 154, 156. Through the use of an organic chemical which has an index of refraction change rate temperature, a change of temperature of the plates and the organic liquid by several degrees Celsius, using a thermoelectric (TE) device of low power, the Fabry Perot cavity can be tuned uniformly without moving parts or piezoelectric crystals.

For example, ethanol, acetone and many other organic chemicals have an index of refraction change rate with temperature at 20° C., which is at least −0.0042 per °C. The temperature change of the liquid will change the wavelength between the etalon plates 154, 156 by one entire free spectral range (about 2 nm or one order number) if the temperature is only 6° C., at a wavelength of 700 nm. The temperature required for operation may be found from the equation:

$$\Delta\lambda(\delta T) = ((n)T1 - n(T2)\ (h(T1)) - h(T2))\cos \theta/m.$$

The free spectral range of the plates $\Delta\lambda$(FSR), at any wavelength, $\lambda$ is given by:

$$\Delta\lambda(FSR) = \lambda^2/2 \ mn(T1)h)(T1) \cos \Theta.$$

It is necessary that $\Delta\lambda(\delta T) > \Delta\lambda(FSR)$. In these equations, m is the order of the light fringes, n(T) is the organic liquid index of refraction at the temperatures T, h(T) is the spacing between the Fabry Perot plates 154, 156, as it varies with temperature, and $\Theta$ is the angle between the incident light and the optic axis of the plates.

The liquid placed between the plates is chosen so that its index of refraction decreases with increased temperature. This is done because the separation of plates 154, 156, t, will increase only slightly with temperature. The thermal expansion coefficient of fused silica is about 10(−7) cm/cm degree Celsius.

The changing plate separation is both small and adds to the tuning, since the increasing temperature expands the silicon and reduces the plate separation.

Because the Fabry Perot plates are small in dimension, for example, 3 cm×2 cm, they have a small mass and hence a thermoelectric cooler 160 having a power of about 15 watts is sufficient to tune the plates 154, 156 by one free spectral range in a few seconds. The thermoelectric cooler 160 may be of conventional design and controlled by a power supply 102, as indicated in FIGS. 2 and 3.

Another option for the tunable wavelength filter is to use a material with a high thermoelectric optical coefficient such as, for example, ZnS, AgGaS$_2$, LiIO$_3$, BGO, ADP and KN$_6$O$_3$ for the etalons 154, 156. Such solid inorganic materials have an index of refraction that changes rapidly with temperature at about 20° C. These crystals are available from CSK Optronics or Skytek Corporation.

Most of the materials can be tuned over one free spectral range with a temperature change of less than 10° C. This temperature range is easily accomplished with the thermoelectric device through the power supply 102 which may be, of course, computer-controlled. The temperature may be monitored with a silicon thermistor to an accuracy of 0.01° C. and in this instance, the required temperature change to tune the Fabry Perot 152 by one free spectral range is:

$$\Delta T = n(d\lambda/\lambda)_{FSR}/(dn/dT + n(dh/dT)$$

where $(d\lambda/\lambda)_{FSR}$ is the free spectral range of the Fabry Perot etalon $=\lambda/2nh$, dn/dT is the thermal optical coefficient of the etalon material, n is the index of refraction of the etalon material and (dh/dT) is the thermal expansion coefficient. Suitable Fabry Perot filters may be obtained from either Melles Griot or Burleigh Instruments.

Alternatively, a high resolution acousto-optical tunable filter may be utilized with a bandpass of about 40 cm$^{-1}$ which is approximately constant with wave number. Such AOT filters are available from Brimose of Baltimore, Md., and are a perfect match to the chosen plate separation. Suitable AOTFs have a band pass that scale with wavelength as 1$\lambda^2$, similar to the Fabry Perot plates 154, 156.

The broad band filter 90 may also be an AOTF or one or more ZnSe prisms 166, 168. Two or more of the prisms 166, 168 may be utilized in tandem to isolate a single value m or order of the light fringes (not shown) emitted by the Fabry Perot 152. Suitable prisms 166, 168 are available from II–VI Corporation and have a principal advantage in their high spectral dispersion, $dn/d\lambda$. Another advantage of such prisms is their ability to enable observations of many orders, m, of the Fabry Perot plates 154, 156 simultaneously. Alternatively, an AOTF may be utilized in lieu of the prisms 166, 168. However, they are not as economical as the ZnSe prisms.

With regard to the prisms 166, 168, the reciprocal spectral dispersion, $dy/d\lambda$ is given by the equation:

$$dy(ZSP)/d\lambda = F_m dn/d\lambda)B/b$$

where $F_m$ is the focal length of the collecting lens in cm, B is the prism wavelength and b is the open aperture of the beam entering the prism front face.

Suitable prisms 166, 168 will have a base-to-aperture ratio of B/b of 1.72. This ratio implies an equilateral (60°) prism, and also requires that b=2 cm to accommodate the aperture of the Fabry Perot etalons. The differential refractive index of ZnSe, $dn/d\lambda$, varies from 0.994/micron at 0.54 micron to 0.386/micron at 0.74 micron. This variation makes the ZnSe prism reciprocal dispersion about 111 micron/nm at 0.54 micron and about 84 micron/nm at 0.74 micron. To calculate this reciprocal dispersion, it is assumed the focal length of the detector collector lens, $F_m$, is only 6 cm.

The Fabry Perot reciprocal spectral dispersion over one order can be computed with the equation:

$$dy(FP)/dm = F_m \tan \theta_2$$

where $\theta_2 = \arccos((m-1) \cos \theta_1/m)$, and m is given by (2a) or $m = 2 nt/\lambda$ if $\cos \theta_1 = 1$. If $\cos \theta_1 = 1$ (for the central fringe), then the linear spacing to the next fringe is about 0.32 cm at 0.56 micron and about 0.36 cm at 0.74 micron. These results imply a spatial resolution element of about 100 microns if the etalon finesse is 30.

This number closely matches the spectral dispersion of the ZnSe prisms 166, 168 per nanometer. The dispersion relation between prisms 166, 168 and etalons 154, 156 ensures that ta 256 element linear array diode (LAD) detector (not shown) can function at both the high and low resolution by a simple 90° rotation of the array. If no movement is required, two-dimension cooled charge coupled device 96 may be utilized to view the fringes directly. This feature will enable simultaneous high and low resolution measurements. The CCD detector array 95 together with a video board in the data processor 114 to survey the spectrum at low, or 1 nm resolution, and also to display the stronger spectral lines at a high spectral resolution of about 0.05 nm.

Suitable two-dimensional cooled charge coupled devices 96, 98 are available from Hamamatsuf or EG&G, Reticon.

In summary, the monitor in accordance with the present invention can access all wavelengths from 500 to 4,000 nm with no moving parts. This design will require a 100 micron aperture stop at the position marked S on FIG. 2 to separate the Fabry Perot orders from different emission lines. The orders will overlap without the aperture, but the CCD two-dimensional array 96, 98 will resolve the fringe overlap. To observe a single spectral line, a linear variable or acousto-optical (AOTF) filter may be used to remove the overlapping. The design has an option (not shown) for the 90° rotation of the LAD detector array to fully access the spectrum for both the Fabry Perot (high) and prism (low) resolution modes. The precise resolution in the high (Fabry Perot) mode is about 1.2 $cm^{-1}$, or 0.05 nm at 700 nm, and in the low (prism) mode about 30 $cm^{-1}$ or 1.2 nm at 700 nm. The CLM2 and the CLMSW instruments will each require a different laser.

Although there has been hereinabove described a monitor and method in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A compact laser diode monitor for measuring concentrations of individual atomic and molecular species in both gaseous and semitransparent fluids, the monitor comprising:

first diode laser means for exciting a first selected electronic transition of a specific atomic or molecular species of a sample, said first laser means having a first frequency output resonant with the first selected electronic transition;

second diode laser means for exciting a second selected electronic transition of said specific atomic or molecular species of said sample, said second laser means having a second frequency output resonant with the second selected electronics transition, a difference between said first and second frequency outputs being equal to a vibrational energy level difference of the specific atomic or molecular species;

means for simultaneously directing said first and second frequency outputs into said sample, with selected momentum vectors in order to cause the selected atomic or molecular species to emit a coherent photon signal in a selected direction having a frequency equal to twice the first frequency output minus the second frequency output; and means for detecting the emitted coherent photon signal and spectrally analyzing the emitted coherent photon signal.

2. The monitor according to claim 1 wherein the means for directing said first and second frequency outputs into said sample comprises lens means for causing said first and second frequency outputs to converge onto said sample.

3. The monitor according to claim 2 wherein the means for directing said first and second frequency outputs into said sample further comprising mirror means for causing first and second frequency outputs passing through the sample to reenter the sample a selected number of times.

4. The monitor according to claim 3 wherein the selected number of times is at least 50.

5. The monitor according to claim 4 wherein said lens means and mirror means are spaced apart from one another no more than 2 centimeters.

6. The monitor according to claim 2 further comprising optical means, disposed between said sample and the means for detecting, for reducing fluorescent signal, generated by said sample, entering said means for detecting the emitted coherent photon signal.

7. The monitor according to claim 6 wherein said means for detecting the emitted coherent photon signal comprises a tunable wavelength filter.

8. The monitor according to claim 7 wherein the tunable wavelength filter is tunable by application of heat thereto.

9. The monitor according to claim 8 wherein said tunable wavelength filter comprises a Fabry Perot device having two spaced apart flat parallel plates with an inorganic chemical disposed between the plates, said organic chemical having an index of refraction change rate with temperature.

10. The monitor according to claim 9 wherein said inorganic chemical has an index of refraction decreasing with increasing temperature.

11. The monitor according to claim 8 wherein said tunable wavelength filter comprises a Fabry Perot device having two spaced apart flat parallel plates, comprising a solid inorganic material, said solid inorganic material having an index of refraction change rate with temperature.

12. The monitor according to claim 9, 10 or 11 further comprising thermoelectric heater means for tuning the Fabry Perot device.

13. The monitor according to claim 9 wherein said means for detecting the emitted coherent photon signal comprises detector array means for receiving the selected Fabry Perot fringe, and producing an electrical signal corresponding thereto.

14. The monitor according to claim 13 wherein said means for detecting the emitted coherent photon signal comprises detector array means for receiving the selected Fabry Perot fringe and producing an electrical signal corresponding thereto.

15. The monitor according to claim 13 wherein said means for detecting the emitted coherent photon signal comprises detector array means for receiving one of the Fabry Perot fringes and the selected fringe and producing electrical signals corresponding thereto.

16. The monitor according to claim 9 wherein said means for detecting the emitted coherent photon signal comprises broadband filter means for isolating a single order of fringe output of the Fabry Perot device.

17. The monitor according to claim 16 wherein said broadband filter means comprises an acousto-optic tunable filter.

18. A compact laser diode monitor for comparing concentrations of individual atomic and molecular species in both gaseous and semitransparent fluids, the monitor comprising:
   first diode laser means for exciting a first selected electronic transition of a specific atomic or molecular species of a sample and a standard, said first laser means having a first frequency output resonant with the first selected electronic transition;
   second diode laser means for exciting a second selected electronic transition of said specific atomic or molecular species of said sample and the standard, said second laser means having a second frequency output resonant with the second selected electronics transition, a difference between said first and second frequency outputs being equal to a vibrational energy level difference of the specific atomic molecular species;
   means for simultaneously directing said first and second frequency outputs into said sample and standard with selected momentum vectors in order to cause the selected atomic or molecular species in the sample and standard to emit coherent photon signals in selected directions having a frequency equal to twice the first frequency output minus the second frequency output; and
   means for detecting the emitted coherent signals and comparing same.

19. The monitor according to claim 18 wherein the means for directing said first and second frequency outputs into said sample comprises lens means for causing said first and second frequency outputs to converge onto said sample and standard.

20. The monitor according to claim 19 wherein the means for directing said first and second frequency outputs into said sample further comprising mirror means for causing first and second frequency outputs passing through the sample to reenter the sample and standard a selected number of times.

21. The monitor according to claim 20 wherein the selected number of times is at least 50.

22. The monitor according to claim 21 wherein said lens means and mirror means are spaced apart from one another no more than 2 centimeters.

23. The monitor according to claim 19 further comprising optical means, disposed between said sample and standard and the means for detecting, for reducing fluorescent signal, generated by said sample, entering said means for detecting the emitted coherent photon signals.

24. The monitor according to claim 23 wherein said means for detecting the emitted coherent photon signal comprises a tunable wavelength filter.

25. The monitor according to claim 24 wherein the tunable wavelength filter is tunable by application of heat thereto.

26. The monitor according to claim 25 wherein said tunable wavelength filter comprises a Fabry Perot device having two spaced apart flat parallel plates with an organic chemical disposed between the plates, said organic chemical having an index of refraction change rate with temperature.

27. The monitor according to claim 26 wherein said organic chemical has an index of refraction decreasing with increasing temperature.

28. The monitor according to claim 25 wherein said tunable wavelength filter comprises a Fabry Perot device having two spaced apart flat parallel plates, comprising a solid inorganic material, said solid inorganic material having an index of refraction change rate with temperature.

29. The monitor according to claim 26, 27 or 28 further comprising thermoelectric heater means for tuning the Fabry Perot device.

30. The monitor according to claim 26 wherein said means for detecting the emitted coherent photon signal comprises dispersive means, disposed for receiver output from the tunable wavelength filter, for selecting Fabry Perot fringes in the output for viewing.

31. The monitor according to claim 30 wherein said means for detecting the emitted coherent photon signals comprises detector array means for receiving the selected Fabry Perot fringes and producing electrical signals corresponding thereto.

32. The monitor according to claim 30 wherein said means for detecting the emitted coherent photon signals comprises detector array means for receiving one of the Fabry Perot fringes and the selected fringe and producing electrical signals corresponding thereto.

33. The monitor according to claim 26 wherein said means for detecting the emitted coherent signals comprises broadband filter means for isolating a single order of fringe output of the Fabry Perot device.

34. The monitor according to claim 33 wherein said broadband filter means comprises an acousto-optic tunable filter.

35. A method for monitoring concentrations of individual atomic and molecular species in both gases and semitransparent fluids, said method comprising the steps of:
   directing a first laser having a frequency resonant with a first selected electronic transition of a specific atomic or molecular species into a sample comprising the specific atomic or molecular species;
   simultaneously directing a second laser into said sample in order to cause the selected atomic or molecular species to emit a coherent photon signal in a selected direction, said second laser having a frequency resonant with a second selected electronic transition of the specific atomic or molecular species, a difference between said first and second laser resonant frequencies being equal to a vibrational energy level difference of the specific atomic or molecular species; and detecting the emitted coherent photon signal.

36. The method according to claim 35 further comprising the step of directing the first and second lasers into the sample with vector momentums causing the selected atomic or molecular species to emit the coherent photon signal in the selected direction.

* * * * *